United States Patent [19]

Firth et al.

[11] Patent Number: 4,538,008

[45] Date of Patent: Aug. 27, 1985

[54] PREPARATION OF ORTHO-ALKYLATED PHENOLS

[75] Inventors: Bruce E. Firth, Arlington Heights, Ill.; Terry J. Rosen, Berkeley, Calif.

[73] Assignee: UOP Inc., Des Plaines, Ill.

[21] Appl. No.: 602,302

[22] Filed: Apr. 20, 1984

Related U.S. Application Data

[63] Continuation-in-part of Ser. No. 440,676, Nov. 10, 1982, Pat. No. 4,447,652.

[51] Int. Cl.$^3$ .................. C07C 37/00; C07C 39/06
[52] U.S. Cl. .................................. 568/783; 568/784
[58] Field of Search ............... 568/780, 783, 784, 627

[56] References Cited

U.S. PATENT DOCUMENTS

| | | | |
|---|---|---|---|
| 2,289,886 | 7/1942 | Schmerling | 260/621 |
| 3,342,750 | 9/1967 | Kearby | 252/437 |
| 3,655,780 | 4/1972 | Kohn et al. | 568/783 |
| 4,202,798 | 5/1980 | Johnson et al. | 252/437 |
| 4,283,571 | 8/1981 | Keim et al. | 568/783 |
| 4,283,572 | 8/1981 | Klicker | 568/783 |
| 4,447,657 | 5/1984 | Firth et al. | 568/783 |
| 4,465,871 | 8/1984 | Firth et al. | 568/783 |

FOREIGN PATENT DOCUMENTS 2345911  3/1975  Fed. Rep. of Germany ...... 568/783

OTHER PUBLICATIONS

Dewar et al., "Jour. Chem. Soc.", (1960), pp. 959–963.

Primary Examiner—Werren B. Lone
Attorney, Agent, or Firm—Thomas K. McBride; William H. Page, II; Eugene I. Snyder

[57] ABSTRACT

Secondary or tertiary alkyl phenyl ethers may be induced to undergo thermal rearrangement on alumina, aluminum phosphate, or a silica-modified alumina as catalyst to afford the isomeric ortho-alkylphenol. Such rearrangement generally occurs under milder conditions than does the alkylation of a phenol with an olefin using the same alumina as an alkylating catalyst with high regioselectivity and good control over the extent of alkylation.

15 Claims, No Drawings

PREPARATION OF ORTHO-ALKYLATED PHENOLS

CROSS-REFERENCE TO RELATED APPLICATION

This application is a continuation in-part of our copending application, Ser. No. 440,676, filed Nov. 10, 1982, now U.S. Pat. No. 4,447,652, all of which is incorporated by reference.

BACKGROUND OF THE INVENTION

Alkylphenols are materials of commerce desirable for their antioxidant properties. Many members of this class have commercial utility in such applications as antioxidants and stabilizing agents for fuel oils and antioxidants for food of diverse type. Among the phenols which are antioxidants the ortho-alkyl and ortho, ortho-dialkylphenols appear to be superior. That is to say, the ortho-alkylphenols and ortho, ortho-dialkylphenols seem to be better antioxidants than their isomers. There is a corresponding need to prepare such ortho-alkylated phenols with relatively high selectivity and yield.

The usual method of preparing alkylphenols is to alkylate phenols with an olefin, alkyl halide, or alcohol in the presence of an alkylating catalyst which generally is a Lewis acid. Catalysts which have been employed include strong inorganic acids (sulfuric acid, phosphoric acid, and hydrofluoric acid to name a few), strong organic acids (for example, sulfonic acids and cationic exchange resins bearing such acid functionalities), metal halides (boron trifluoride, aluminum halides, and zinc halides are exemplary) and inorganic oxides such as alumina and silica. A deficiency in all such methods is their limited selectivity for ortho-alkylation, that is, alkylation at available ortho positions occurs with only limited preference to alkylation at other available positions. Another limitation in such methods is that some 2,4-dialkylphenols undergo further alkylation to 2,4,6-trialkylphenols only with great difficulty, if at all. Still another disadvantage is the relatively high reaction temperature necessary where the more selective alkylating catalysts are used, for example, inorganic oxides.

Some instances of the rearrangement of alkyl phenyl ethers to the isomeric alkylphenol have been reported. For example, U.S. Pat. No. 2,289,886 discloses that alkyl phenyl ethers when treated with hydrogen fluoride afford both the isomeric alkylphenol and the dealkylated phenol. More recently U.S. Pat. No. 4,283,572 describes the rearrangement of nonyl phenyl ether to a mixture of phenol, mononoylphenol, and dinonylphenol. The patentee in German Pat. No. 2,345,911 teaches the gas phase rearrangement of phenetole at 270°–320° C. over an alumina activated with sulfur trioxide, a strong Lewis acid, with the regioselectivity falling short of that observed in this invention. By "regioselectivity" is meant selectivity in the site of the aromatic ring to which the ether group migrates. Such sparse reports are in marked contrast to the well known thermal rearrangement of allyl phenyl ethers to allyl phenols (Claisen rearrangement) where the allyl group migrates selectively to an ortho or, less often, to a para position.

We have made the remarkable discovery that alkyl phenyl ethers undergo a thermal rearrangement in the presence of an alumina as catalyst to afford the isomeric ortho-alkylphenols with high yield and good selectivity. Not only is the thermal rearrangement of an alkyl phenyl ether to an alkylphenol as a general phenomenon without precedent, but the regioselectivity of the rearrangement to afford an ortho-alkylphenol is completely surprising.

Such a method of ortho-alkylating phenols has many advantages over the prior art methods. One advantage is formation of the ortho-alkylphenol at a substantially lower temperature than was previously possible. That is to say, the rearrangement occurs at a temperature lower than that necessary for alkylation of the phenol with, for example, an olefin using alumina as the alkylating catalyst. Since the alkyl phenyl ether may be prepared from a phenol under relatively mild conditions, our discovery makes possible a two-stage preparation of an alkylphenol via (1) formation of the alkyl phenyl ether followed by (2) rearrangement of the ether, both reactions proceeding under substantially milder conditions than direct alkylation of the phenol.

Another advantage of the invention described herein is its high regioselectivity in affording ortho-alkylated phenols. Thus, the prior art alkylating methods afford ortho-alkylated materials with varying selectivity, whereas the method we describe below affords ortho-alkylated products with substantially improved selectivity.

Still another advantage of the method which is our invention is that it affords products which sometimes are not otherwise readily available. For example, (2-alkylphenyl) alkyl ethers undergo rearrangement to the isomeric 2,6-dialkylphenol with great specificity, whereas direct alkylation of the corresponding 2-alkylphenol may fail to afford the desired 2,6-dialkylphenol, or do so only in relatively poor yield.

Yet another advantage of our method is the control it affords over the extent of alkylation. Rearrangement of secondary and tertiary alkyl phenyl ethers as described results in only the secondary or tertiary alkyl group being introduced into the aromatic nucleus. This is tantamount to monoalkylation of the parent phenol, where, contrastingly, traditional methods of alkylating phenols typically leads to polyalkylation.

SUMMARY OF THE INVENTION

An object of the invention described herein is to prepare ortho-alkylphenols by rearrangement of the isomeric secondary and tertiary alkyl phenyl ethers. One embodiment is a method of rearrangement which is thermally induced on alumina as a catalyst. In a more specific embodiment the temperature is from about 75° C. to about 175° C.

Another object of our invention is to alkylate phenols selectively at the ortho position by converting the phenol to a secondary or tertiary alkyl phenyl ether and rearranging the latter in a thermal reaction on an alumina catalyst. In a specific embodiment the reactant phenol is a 2-alkylphenol and the product is a 2,6-dialkylphenol.

DESCRIPTION OF THE INVENTION

In one aspect the invention described herein is a method of rearranging a secondary or tertiary alkyl phenyl ether to the isomeric ortho-alkylphenol comprising heating said ether in contact with alumina, aluminum phosphate, or silica-modified alumina under rearrangement conditions and recovering the ortho-alkylphenol. In another aspect our invention is a method of ortho-alkylating a phenol comprising converting the phenol to an alkyl phenyl ether, thermally rearranging the ether in the presence of one of the aforementioned catalysts, and recovering the formed ortho-alkylphenol.

We have found that alkyl phenyl ethers can be induced to undergo thermal rearrangement in contact with an alumina. The alkyl group may be an unsubstituted alkyl, i.e., $C_nH_{2n+1}$, or it may be a substituted alkyl group where the substituent is otherwise inert under the reaction conditions. Examples of inert substituents include the halogens, a substituted or unsubstituted amino group, an aryl moiety, esters, the nitro group, and so forth. In this specification it is to be understood that the term "alkyl" refers both to unsubstituted and substituted alkyl groups.

Secondary and tertiary alkyl groups are preferred. Except for benzyl and similar arylmethyl groups, primary alkyl groups rearrange with difficulty, often with isomerization of the alkyl group itself, thereby limiting their utility in this invention. Examples of suitable alkyl groups include propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, benzyl, and so forth.

The aromatic portion of the alkyl phenyl ethers of this invention may be the unsubstituted phenyl group itself, but in the more usual case the aromatic ring contains one or more groups which are otherwise inert, subject to the provision that at least one ortho position remains unsubstituted. Examples of inert ring substituents include the halogens, and the nitro, ester, hydroxy, alkoxy, and alkyl groups. Alkyl and alkoxy substituents are especially important. A ring substituted alkyl group may be the same or different from the alkyl portion of the ether and may occupy any of the ring positions, but 2-alkylphenyl alkyl ethers are especially desirable reactants. The most desirable ring-substituted alkyl groups are those containing up to about 10 carbon atoms. Examples include methyl, ethyl, propyl, butyl, pentyl, hexyl, heptyl, octyl, nonyl, and decyl groups. Illustrative examples of the aromatic portion of the alkyl phenyl ethers of this invention include 2-methylphenyl, 3-methylphenyl, 4-methylphenyl, 2,4-dimethylphenyl, 2-ethylphenyl, 4-ethylphenyl, 2-n-propylphenyl, 3-n-propylphenyl, 2-i-propylphenyl, 4-i-propylphenyl, 2,4-i-propylphenyl, 2-i-propyl-4-methylphenyl, 2-t-butylphenyl, 4-t-butylphenyl, 2-t-butyl-4-methylphenyl, 2-methyl-4-t-butylphenyl, the isomeric pentylphenyls, hexylphenyls, heptylphenyls, and so on.

Of particular interest are those alkyl phenyl ethers where the aromatic ring bears an alkoxy or hydroxy moiety. The alkoxy moiety is a powerful ortho directing group in alkylation, so that alkylation of, e.g., a 4-alkoxyphenol generally leads to a mixture representing alkylation ortho to the alkoxy moiety as well as alkylation ortho to the phenolic hydroxyl. Contrastingly, rearrangement of a secondary or tertiary alkyl phenyl ether according to our invention occurs with great regioselectivity, leading to introduction of the alkyl group virtually exclusively ortho to the oxygen whence it originated. Although such regioselectivity may be unimportant where the aromatic ring bears a hydroxy moiety, our method remains important for such compounds because it assures introduction of but one alkyl group into the ring. This is equivalent to monoalkylation of a dihydric phenol, which generally is difficult because activation of the aromatic ring by two hydroxy groups normally leads to dialkylation.

Thus, among favored reactants in our method are secondary or tertiary alkyl alkoxyphenyl ethers, or secondary or tertiary alkyl hydroxyphenyl ethers, and especially the 4-alkoxyphenyl and 4-hydroxyphenyl ethers which afford as products 2-alkyl 4-alkoxyphenols and 2-alkyl-4-hydroxyphenols, respectively. In those cases where the reactant is an alkoxyphenyl ether it is desirable that the alkyl portion of the alkoxy moiety be a primary alkyl group so it will not undergo rearrangement competititvely with the secondary or tertiary alkyl portion of the ether. With this limitation in mind the alkyl portion of the alkoxy moiety has the same general description given above for ring alkyl substituents. Illustrative examples of suitable substrates include t-butyl methoxyphenyl ether, i-propyl ethoxyphenyl ether, i-butyl propoxyphenyl ether, 2-methyl2-butyl pentyloxyphenyl ether, 2-pentyl hydroxyphenyl ether, 1-butyl-hydroxyphenyl ether, i-propyl hydroxyphenyl ether, 3-pentyl nonyloxyphenyl ether, and so forth.

The alkyl phenyl ethers of this invention are caused to undergo a thermally induced rearrangement in contact with alumina, aluminum phosphate, or silica-modified alumina. Although the various forms of alumina may be used in this invention, not necessarily with equivalent results, gamma-alumina is the preferred choice. By aluminum phosphate is meant materials such as those disclosed in U.S. Pat. Nos. 3,342,750 and 4,202,798.

In contrast to the usual silica alumina, which is a copolymer of silica and alumina formed from silica and alumina monomers and which is characterized by aluminum-oxygen-silicon bonds throughout the matrix, the silica-modified alumina of this invention results from the interaction of a silicon monomer with an alumina polymer, thereby forming aluminum oxygen-silicon bonds only at the exposed surface of the material in a very systematic manner. The silica-modified alumina is prepared by depositing a monomeric silicon compound on the surface of an alumina, then converting the silicon compound to silica by calcination in air. Examples of suitable monomeric silicon compounds include organosilanes such as tetralkylsilanes, tetraarylsilanes, $R_4Si$ and $Ar_4Si$, and analogous siloxanes, $(RO)_4Si$ and $(ArO)_4Si$. Conversion of the silicon monomer to silica is effected by calcination in air, typically at temperatures between about 600° F. and about 1200° F., but more generally at a temperature and for a time such that the underlying alumina structure remains unaffected. Silica-modified alumina as used in this invention contains from about 0.5 to about 25% silicon, usually between about 1 to about 10% silicon.

The amount of catalyst used in the practice of this invention depends upon the nature of the alkyl group, that is, whether secondary or tertiary, and the rate of rearrangement desired. When the reaction is run in a batch mode the amount of alumina used may vary from about 0.1 to over 100% by weight relative to the ether to be rearranged.

The ether is contacted with an alumina under rearrangement conditions. The temperature at which rearrangement occurs may be from about 75° C. to about 175° C. depending upon the nature of the alkyl group. It has been found that a tertiary group undergoes rearrangement substantially more readily than does a secondary alkyl group. Where a secondary alkyl group undergoes rearrangement a temperature from about 140° C. to about 175° C. generally suffices; where a tertiary alkyl group rearranges the temperature may be from about 75° C. to about 140° C. Since pressure has no important effect on this reaction rearrangement generally is performed under autogenous pressure.

Conversion of phenols to alkyl phenyl ethers may be performed by any method known in the art. For example, the phenol can be converted to its phenoxide which is then reacted with an alkyl halide, often in a relatively polar solvent. Another example of a preparative route is the reaction of a phenol with an alcohol in the presence of an acid catalyst, such as a strong inorganic acid or a cationic exchange resin bearing sulfonic acid groups. Still another preparative route is the reaction of a phenol with an olefin in the presence of a Lewis acid, such as an inorganic oxide as alumina or a metal halide. It is to be understood that the conversion of a phenol to its alkyl phenyl ether is well known in the art and need not be described here in any great detail.

The following examples are illustrative of this invention and are not to be construed as limiting the invention thereto.

EXAMPLE 1

Aluminum phosphate used in the practice of this invention may be prepared generally as described by Johnson and Erickson in U.S. Pat. No. 4,202,798. The resulting material may contain an atomic ratio of aluminum to phosphorus from about 20:1 to about 1:1, and generally is in the range 5–1:1.

Preparation of silica modified alumina is exemplified by the following description of a 3% silicon on alumina. To 172 g of a preformed alumina sphere was added a solution of 39.4 g tetraethyl orthosilicate in enough toluene to make 175 ml of solution. The mixture is rotated for 0.5 hour to ensure adequate contact, after which toluene is removed by evaporation at reduced pressure. The resulting dried solid is calcined in air for 1 hour at 350° C., then for 1 hour at 600° C.

EXAMPLE 2

The following description is representative of the rearrangement of an alkyl phenyl ether. A mixture of 15 g isopropyl (2-isopropylphenyl) ether and 5 g of catalyst (gamma-alumina, silica-modifed alumina, or aluminum phosphate) in a 300 ml stirred autoclave under nitrogen may be heated for 2–6 hours with stirring. After the reaction mixture has cooled to room temperature a solvent such as acetone may be added and the mixture filtered. Solvent may be removed by evaporation, under reduced pressure if desired, and the formed 2,6-diisopropylphenol may be isolated by fractional distillation.

What is claimed is:

1. A method of rearranging a secondary alkyl or tertiary alkyl phenyl ether to an ortho-alkylphenol, where the alkyl group contains from 3 to about 20 carbon atoms, comprising contacting said ether with alumina, aluminum phosphate, or a silica-modified alumina at a temperature from about 75° C. to about 175° C. and recovering the orthoalkyl phenol.

2. The method of claim 1 where both ortho-positions of the aromatic ring in the ether are occupied by hydrogen.

3. The method of claim 1 where the ether is a (2-alkylphenyl) alkyl ether.

4. The method of claim 1 where the ether is an isopropyl ether.

5. The method of claim 1 where the ether is a tertiary butyl ether.

6. Th method of claim 1 where contacting is with alumina.

7. The method of claim 1 where contacting is with aluminum phosphate.

8. The method of claim 1 where contacting is with a silica-modified alumina.

9. A method of ortho-alkylating a phenol comprising converting the phenol to an alkyl phenyl ether where said alkyl is a secondary or tertiary alkyl moiety containing from 3 to about 20 carbon atoms, heating the ether in the presence of a catalyst selected from the group consisting of alumina, aluminum phosphate, and silica-modified alumina at a temperature from about 75° C. to about 175° C., and recovering the formed ortho-alkylphenol.

10. The method of claim 9 where the phenol is a 2-alkylphenol.

11. The method of claim 9 where the ether is an isopropyl ether.

12. The method of claim 9 where the ether is a tertiary butyl ether.

13. The method of claim 9 where contacting is with aluminum phosphate.

14. The method of claim 9 where contacting is with alumina.

15. The method of claim 9 where contacting is with a silica-modified alumina.

* * * * *